US012680966B2

(12) United States Patent
Moran et al.

(10) Patent No.: US 12,680,966 B2
(45) Date of Patent: Jul. 14, 2026

(54) METHOD FOR NON-CONTACT GROUND MOISTURE LEVEL ESTIMATION AT VARIOUS DEPTHS USING REFLECTED ENERGY AT A WORK MACHINE

(71) Applicant: Deere & Company, Moline, IL (US)

(72) Inventors: Mark D. Moran, Champaign, IL (US); Nathan Ogden, Champaign, IL (US); Chad A. Ackerman, Champaign, IL (US)

(73) Assignee: Deere & Company, Moline, IL (US)

( * ) Notice: Subject to any disclaimer, the term of this patent is extended or adjusted under 35 U.S.C. 154(b) by 312 days.

(21) Appl. No.: 18/592,778

(22) Filed: Mar. 1, 2024

(65) Prior Publication Data

US 2025/0277753 A1     Sep. 4, 2025

(51) Int. Cl.
| | |
|---|---|
| *G01N 22/04* | (2006.01) |
| *A01B 79/00* | (2006.01) |
| *A01B 79/02* | (2006.01) |
| *A01G 25/16* | (2006.01) |
| *G01N 33/24* | (2006.01) |

(52) U.S. Cl.
CPC ........... *G01N 22/04* (2013.01); *A01B 79/005* (2013.01); *A01B 79/02* (2013.01); *A01G 25/167* (2013.01); *G01N 33/246* (2013.01)

(58) Field of Classification Search
CPC .... G01N 22/04; G01N 33/246; A01B 79/005; A01B 79/02; A01G 25/167
See application file for complete search history.

(56) References Cited

U.S. PATENT DOCUMENTS

| | | | |
|---|---|---|---|
| 7,135,871 | B1 | 11/2006 | Pelletier |
| 8,417,192 | B2 | 4/2013 | Brady et al. |
| 9,538,714 | B2 | 1/2017 | Anderson |
| 9,693,496 | B2 | 7/2017 | Tevs et al. |

(Continued)

OTHER PUBLICATIONS

Non-Final Office Action for U.S. Appl. No. 18/592,766, dated Dec. 30, 2025, 23 pages.

(Continued)

*Primary Examiner* — Matthew R Buck
(74) *Attorney, Agent, or Firm* — Gary L. Montle; Lucian Wayne Beavers; Patterson Intellectual Property Law, PC

(57) ABSTRACT

According to a method, model generation includes receiving inputs comprising actual soil properties comprising moisture values at a training ground surface and corresponding ground depths, temperature, surface-RF antenna distance, and antenna vibration. RF signals across a first frequency range are emitted toward the ground surface, and characteristic values determined based on reflected energy. The model is iteratively trained to observe correlations between various inputs and characteristic values at corresponding frequencies. Real-time and non-contact moisture estimation includes corresponding inputs, and a vector network analyzer identifies target frequency ranges as subsets of the first range, and directs RF emittion across the target range toward the ground. Using characteristic values determined from reflected RF signals and further reference to the trained model, moisture values for the current ground surface and corresponding depths are estimated, and an output signal generated for display, control of irrigation, planting depth, etc.

20 Claims, 9 Drawing Sheets

(56)             References Cited

U.S. PATENT DOCUMENTS

| | | | |
|---|---|---|---|
| 9,857,316 B2 * | 1/2018 | Pratt | G01N 22/04 |
| 10,197,378 B2 | 2/2019 | Rhodes et al. | |
| 10,319,050 B2 | 6/2019 | Richt | |
| 10,918,012 B2 | 2/2021 | Rhodes | |
| 10,996,179 B2 | 5/2021 | Wolleben et al. | |
| 11,079,725 B2 | 8/2021 | Palla et al. | |
| 11,191,204 B2 | 12/2021 | Kovach et al. | |
| 11,202,404 B2 | 12/2021 | Walter et al. | |
| 2002/0175849 A1 | 11/2002 | Arndt et al. | |
| 2015/0088785 A1 | 3/2015 | Chi | |
| 2015/0268218 A1 | 9/2015 | Troxler | |
| 2018/0146624 A1 | 5/2018 | Chen et al. | |
| 2018/0224550 A1 | 8/2018 | Guy | |
| 2019/0254222 A1 | 8/2019 | Rhodes | |
| 2020/0229361 A1 * | 7/2020 | Canyon | G01S 13/885 |
| 2020/0281111 A1 | 9/2020 | Walter et al. | |
| 2020/0326716 A1 | 10/2020 | Nichols | |
| 2020/0337232 A1 | 10/2020 | Blank et al. | |
| 2022/0035366 A1 * | 2/2022 | Canyon | G05D 1/0027 |
| 2022/0124960 A1 | 4/2022 | Canyon | |

OTHER PUBLICATIONS

Lewandowski et al.: Article "One-Port VNA Characterization of Soil Dielectric Spectrum" IEEE Transactions on Geoscience and Remote Sensing, vol. 57, No. 6, Jun. 2019.
Wu et al.: Article "Ground-Penetrating Radar Full-Wave Inversion for Soil Moisture Mapping in Trench-Hill Potato Fields for Precise Irrigation" (Nov. 29, 2022) Remote Sensing, 2022 14 6046; https://doi.org/10.3390/rs14236046.

* cited by examiner

| | |
|---|---|
| 820a | ≤ -36.889782 |
| 820b | ≤ -35.520178 |
| 820c | ≤ -34.497728 |
| 820d | ≤ -33.734439 |
| 820e | ≤ -33.164622 |
| 820f | ≤ -32.739236 |
| 820g | ≤ -32.169419 |
| 820h | ≤ -31.40513 |
| 820i | ≤ -30.38368 |

FIG. 8B

| | |
|---|---|
| 810a | ≤ 10.129007 |
| 810b | ≤ 12.66179 |
| 810c | ≤ 14.743822 |
| 810d | ≤ 15.375751 |
| 810e | ≤ 16.740773 |

FIG. 8A

METHOD FOR NON-CONTACT GROUND MOISTURE LEVEL ESTIMATION AT VARIOUS DEPTHS USING REFLECTED ENERGY AT A WORK MACHINE

FIELD OF THE DISCLOSURE

The present disclosure relates generally to work machines having a device mounted thereto for capturing data related to ground moisture, and more particularly to systems and methods utilizing such devices for non-contact moisture estimation based on reflected energy from ground being traversed by work machines, at the surface and at depth.

BACKGROUND

Knowledge of soil moisture levels enables growers to make well-informed management decisions such as adjusting for uniform plant emergence, irrigation frequency, and the measure of other soil properties. Soil moisture greatly impacts germination, plant emergence, and yield. All these traits are agronomically integral for farmers to maximize and having accurate information will enable them to make informed management decisions.

Estimation of soil moisture is important across a wide range of earth working fields, including but not limited to agriculture, earth moving, road building, and turf construction and maintenance. Accordingly, exemplary work machines as discussed herein may include without limitation planters, sprayers, tillers, harvesters, road construction machines, excavators, loaders of various forms, etc.

BRIEF SUMMARY

The current disclosure provides enhancements to conventional soil moisture estimation methods, at least in part by providing a multi-sensor auxiliary unit for work machines capable of estimating surface and depth soil moisture using active radio frequencies. Working on a wide range of soils and conditions, this module allows farmers to make informed management decisions from the cab or otherwise remotely and substantially in real time with respect to traverse of the work area.

One example of such an auxiliary unit may include resident hardware coupled with models and software, collectively designed to be flexible in ascertaining soil moisture along with other soil characteristics such as identifying free and bound water determining plant available water, identifying the quantity and presence of various soil components (clay, organic matter, silt, etc.), and estimate soil physical and chemical characteristics (bulk density, salinity, structure, etc.). A vector network analyzer (VNA) may be utilized as a source of radio frequency (RF) energy further coupled to an antenna which radiates the RF energy outward towards the ground and receives the reflected energy therefrom.

In one particular and exemplary embodiment, a method is disclosed herein for method for non-contact moisture estimation. In a model generation stage, the method includes: receiving first input data representing actual soil properties comprising moisture values at a training ground surface and one or more corresponding ground depths of a respective ground portion; emitting radio signals associated with a first range of frequencies toward the training ground surface, and determining one or more characteristic values for the ground portion based on received reflections of the emitted radio signals; receiving second input data representing temperature, a distance between the training ground surface and a source of the radio signals, and a vibration of the source of the radio signals; and iteratively training a model in data storage comprising correlations between the first data, the one or more characteristic values at corresponding frequencies, and at least a subset of the second data. In a real-time moisture estimation stage, with respect to a current ground surface associated with a current ground portion, the method further includes: receiving third input data representing temperature, a distance between the current ground surface and a source of radio signals, and a vibration of the source of the radio signals; identifying, via a vector network analyzer operatively linked to the source of the radio signals, a target range of frequencies as a subset of the first range of frequencies; emitting radio signals associated with the target range of frequencies toward the current ground portion, and determining one or more characteristic values for the current ground portion based on received reflections of the emitted radio signals; estimating, via the determined one or more characteristic values and further reference to the iteratively trained model, one or more moisture values for the current ground surface and/or one or more corresponding ground depths for the current ground portion; and generating an output signal corresponding to the estimated one or more moisture values.

In one exemplary aspect according to the above-referenced embodiment, the real-time moisture estimation stage may be executed during operation of a work machine traversing a work area comprising a respective current ground surface for each of a plurality of current ground portions.

In another exemplary aspect according to the above-referenced embodiment and optionally further in view of one or more exemplary aspects thereof, the source of the radio signals and one or more sensors configured to provide the third input data may be mounted to a common housing associated with the work machine.

In another exemplary aspect according to the above-referenced embodiment and optionally further in view of one or more exemplary aspects thereof, the output signal may comprise a control signal to one or more actuators for controlling a respective planting depth with respect to each of the plurality of current ground portions, wherein a target planting depth is determined based on the estimated one or more moisture values.

In another exemplary aspect according to the above-referenced embodiment and optionally further in view of one or more exemplary aspects thereof, the target range of frequencies may be determined in the real-time moisture estimation stage based at least in part on a range of expected target planning depths.

In another exemplary aspect according to the above-referenced embodiment and optionally further in view of one or more exemplary aspects thereof, the target planting depth may be further determined based on a stored uniform emergence model correlating the one or more moisture values and expected crop growth at respective planting depths.

In another exemplary aspect according to the above-referenced embodiment and optionally further in view of one or more exemplary aspects thereof, the output signal may comprise a feedback signal to one or more sensors associated with the work machine, or to a controller for determining one or more values based on respective outputs from the one or more sensors and the one or more estimated moisture values.

In another exemplary aspect according to the above-referenced embodiment and optionally further in view of one or more exemplary aspects thereof, the target range of frequencies may be determined in the real-time moisture estimation stage based at least in part on the received third input data.

In another exemplary aspect according to the above-referenced embodiment and optionally further in view of one or more exemplary aspects thereof, the target range of frequencies may be determined in the real-time moisture estimation stage based at least in part on an ascertained configuration of the source of the radio signals and/or a receiver of the radio signals. The radio signals may accordingly be emitted from, and received by, a single antenna or respective antennas in functional communication with the vector network analyzer.

In another exemplary aspect according to the above-referenced embodiment and optionally further in view of one or more exemplary aspects thereof, the model generation stage may be executed at least in part using a first work machine traversing a work area comprising a respective current ground surface for each of a plurality of current ground portions. The real-time moisture estimation stage may further be executed during operation of a second work machine subsequently traversing the work area, wherein the target range of frequencies is determined in the real-time moisture estimation stage based at least in part on measured soil properties for the work area during the model generation stage. The target range of frequencies may for example be determined in the real-time moisture estimation stage based at least in part on mapped soil properties for respective portions of the work area.

In another exemplary aspect according to the above-referenced embodiment and optionally further in view of one or more exemplary aspects thereof, the real-time moisture estimation stage may be executed during operation of a first work machine traversing a work area comprising a respective current ground surface for each of a plurality of current ground portions. The output signal may be provided to a computing device via a communications network, wherein a work plan is generated for the work area based at least in part on the estimated moisture values for each of the plurality of current ground portions, and the work plan provided for utilization by a second work machine associated with the work area.

The output signal may for example comprise a control signal to one or more actuators associated with the second work machine for controlling a respective planting depth with respect to each of the plurality of current ground portions, wherein a target planting depth is determined as part of the work plan. The target range of frequencies may be determined in the real-time moisture estimation stage based at least in part on a range of expected target planning depths. The target planting depth may be further determined based on a stored uniform emergence model correlating the one or more moisture values and expected crop growth at respective planting depths.

The output signal may for example comprise a control signal to one or more actuators associated with the second work machine for controlling a respective irrigation value with respect to each of the plurality of current ground portions, wherein a target irrigation value is determined as part of the work plan.

In another exemplary aspect according to the above-referenced embodiment and optionally further in view of one or more exemplary aspects thereof, the output signal may be provided to a display unit, and a cross sectional view of at least part of the work area is graphically represented on the display unit with indicia representing the one or more moisture values at the respective ground surface and one or more depths.

In another exemplary aspect according to the above-referenced embodiment and optionally further in view of one or more exemplary aspects thereof, the output signal may be provided to a display unit, and an overhead view of at least part of the work area is graphically represented on the display unit with indicia corresponding to relative moisture values for the respective ground portions.

Numerous objects, features, and advantages of the embodiments set forth herein will be readily apparent to those skilled in the art upon reading of the following disclosure when taken in conjunction with the accompanying drawings.

BRIEF DESCRIPTION OF THE DRAWINGS

FIGS. 8A and 8B are graphical diagrams representing indicia for indicating relative moisture levels and reflectance levels, respectively, on a user interface displaying all or part of a work area.

DETAILED DESCRIPTION

With respect to the various figures, one of skill in the art may appreciate that the components thereof are not intended as limiting, are not drawn to scale, and are for illustrative purposes only. For example, the size, dimensions, structural layout, and quantity of the various components with respect to a first embodiment can and will vary in other embodiments unless otherwise specifically noted herein.

Figure 1:
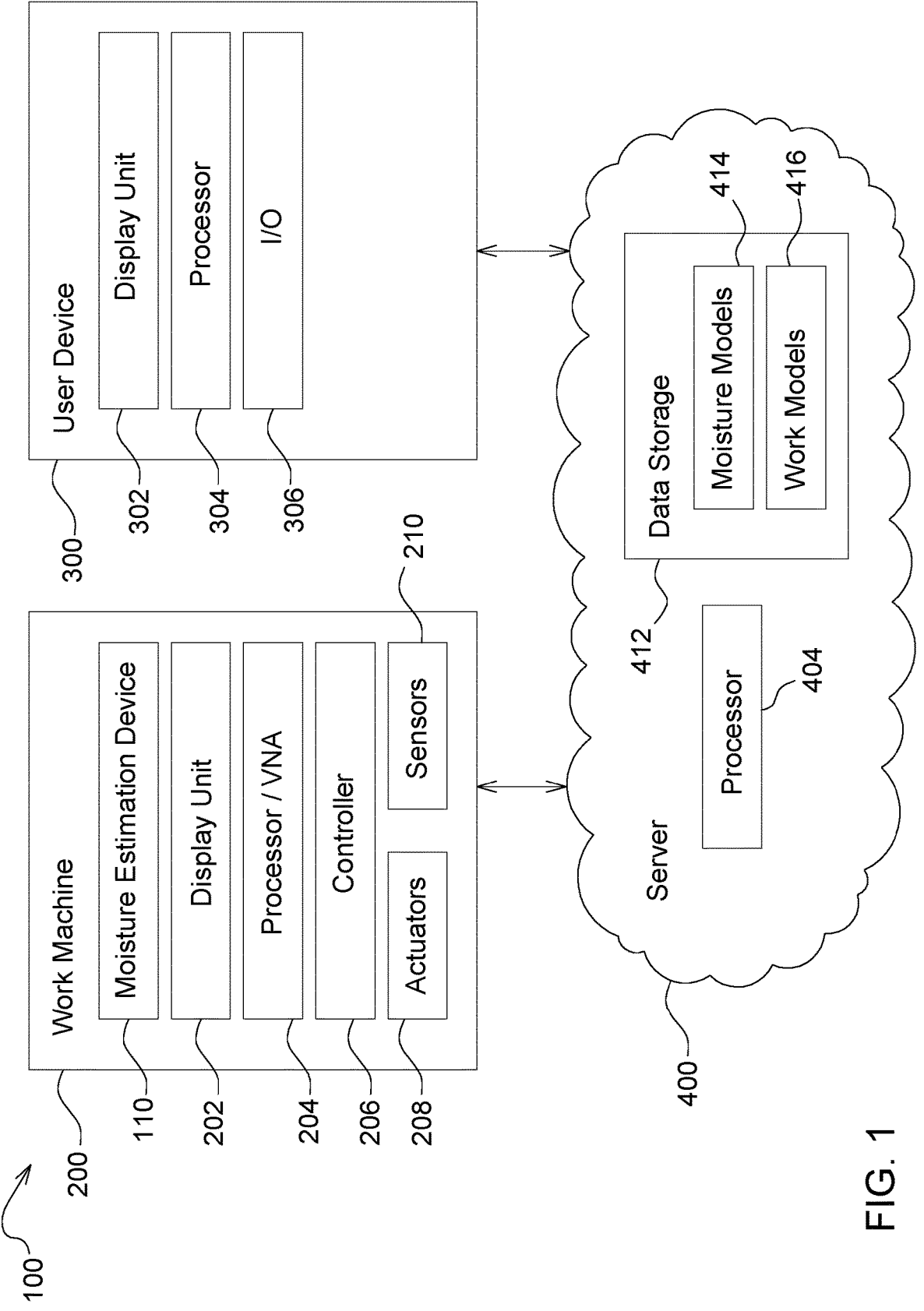
FIG. 1 is a block diagram representing an exemplary non-contact ground moisture estimation system according to an embodiment of the present disclosure.

As represented in FIG. 1, an embodiment of a non-passive ground moisture estimation system 100 as disclosed herein, in total or in relevant and sufficient portions for performing operations and methods as further disclosed herein, may include a work machine 200, one or more mobile computing or other user devices 300, and a remote server 400. In some embodiments, a system and method according to the present disclosure may be self-contained with respect to the work machine 200.

In some embodiments, a modular device 110 (as further described below) may be mounted to or otherwise associated with a work machine 200 as part of a system 100, or the modular device 110 may be configured to independently perform or direct the performance of operations and methods as disclosed herein.

The work machine 200 may further include a display unit 202, for example associated with a local user interface for input/output with respect to a controller 206, various actuators 208, and sensors 210. In various embodiments, the display unit 202 may include a LCD display, a LED display, an OLED display, touch display, or other suitable user interface. The controller 206 may include or otherwise functionally communicate with a vector network analyzer (VNA) 204 or equivalent for implementing the non-contact moisture estimation operations and methods as disclosed herein. The VNA 204 may for example perform radio frequency front-end functionality, for example the measurement of sample scattering parameters, which is then digitized and processed, locally or subsequent to transmission to a downstream processing unit such as moisture estimator 160, controller 206, or the like.

In an exemplary but non-limiting embodiment, VNA 204 may have an available range of 300 kHz to 9 GHz, although preferably only a subset of the available frequency range may be utilized during operation as further described below, and is connected to one or more directional antennas 114 using conventional media such as a coaxial transmission line.

The controller 206 may be part of a machine control system of the working machine, or it may be a separate control module. The controller 206 in the present embodiment is configured to receive input signals from some or all of sensors 210. Various of the sensors 210 may typically be discrete in nature, but signals representative of more than one input parameter may be provided from the same sensor, and one or more sensors 210 as disclosed herein may further include or otherwise refer to signals provided from the machine control system.

Figure 3:
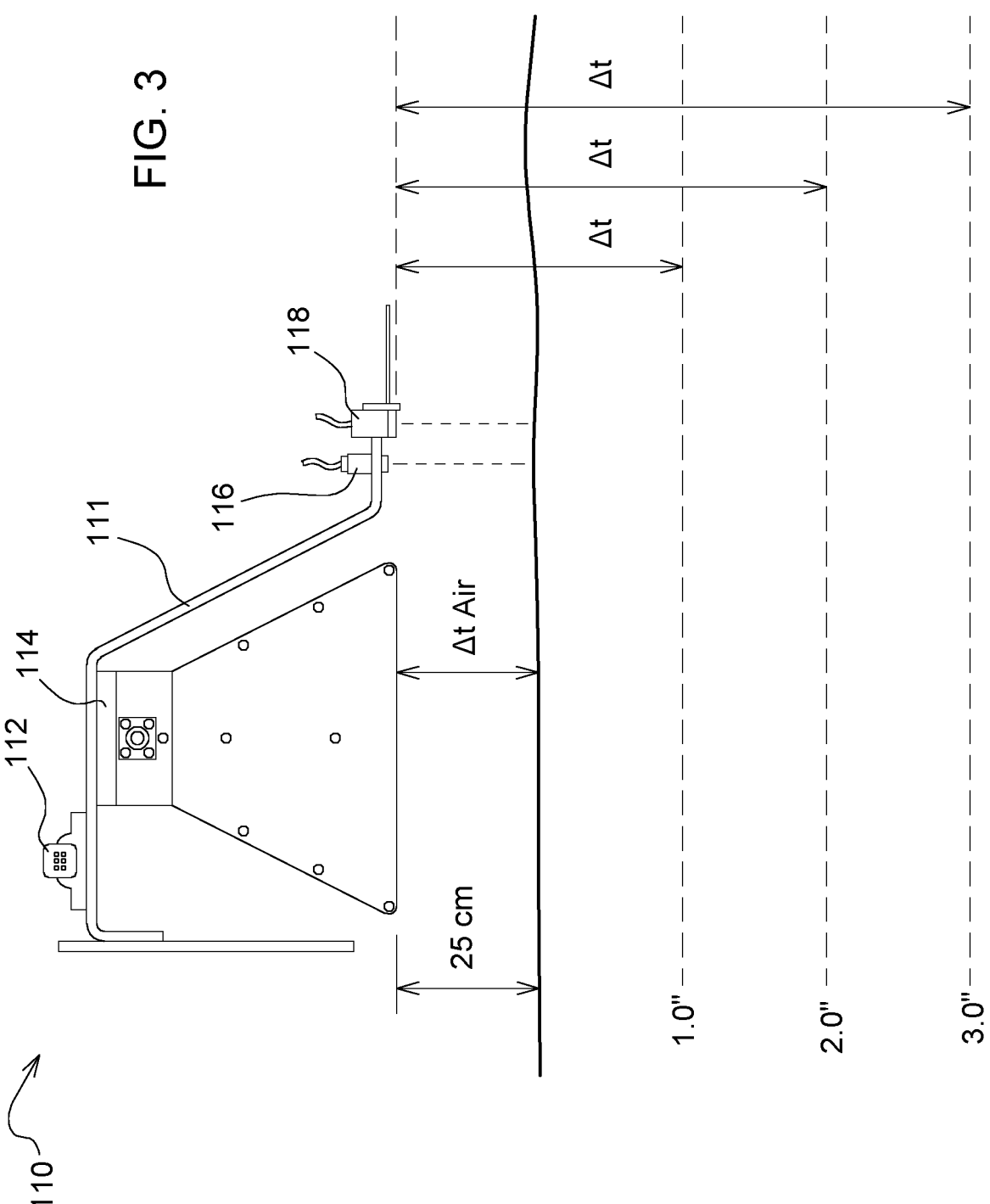
FIG. 3 is a side view representing an exemplary non-contact ground moisture estimation device according to an embodiment of the present disclosure.

The sensors 210 may include sensors associated with the moisture estimation device 110, for example mounted on a housing 111 associated with the device 110 and not directly to the work machine 200 but functionally linked to the VNA 204 and optionally in communication with the controller 206 (if separate). In an embodiment as illustrated in FIG. 3, such sensors may include an inertial measurement unit (IMU) 112, the one or more directional antennas 114, a temperature sensor 116, and a depth/range finding sensor 118.

In an embodiment wherein the moisture estimation device 110 is configured to perform moisture analysis without reliance on a controller 206 of the work machine 200, or at least to perform a portion of the moisture analysis in combination with the controller 206 of the work machine 200, the device 110 may include a controller/processor comprising or otherwise associated with the VNA 204.

In an embodiment the sensors 210 may include machine position determining sensors such as a separate IMU mounted on the work machine 200 itself, and/or a global positioning system (GPS) transceiver 120, ground speed sensors, steering sensors, or the like, or equivalent inputs from the machine control system.

One of skill in the art may appreciate that IMUs are tools that capture a variety of motion- and position-based measurements, including, but not limited to, velocity, acceleration, angular velocity, and angular acceleration. IMUs may include one or more sensors including, but not limited to, accelerometers, which measure (among other things) velocity and acceleration, gyroscopes, which measure (among other things) angular velocity and angular acceleration, and magnetometers, which measure (among other things) strength and direction of a magnetic field. Generally, an accelerometer provides measurements, with respect to (among other things) force due to gravity, while a gyroscope provides measurements, with respect to (among other things) rigid body motion. The magnetometer provides measurements of the strength and the direction of the magnetic field, with respect to (among other things) known internal constants, or with respect to a known, accurately measured magnetic field. The magnetometer provides measurements of a magnetic field to yield information on positional, or angular, orientation of the IMU; similarly to that of the magnetometer, the gyroscope yields information on a positional, or angular, orientation of the IMU. Accordingly, the magnetometer may be used in lieu of the gyroscope, or in combination with the gyroscope, and complementary to the accelerometer, in order to produce local information and coordinates on the position, motion, and orientation of the IMU.

As conventionally known in the art, an accelerometer is an electro-mechanical device or tool used to measure acceleration (m/s$^2$), which is defined as the rate of change of velocity (m/s) of an object. Accelerometers sense either static forces (e.g., gravity) or dynamic forces of acceleration (e.g., vibration and movement). An accelerometer may receive sense elements measuring the force due to gravity. By measuring the quantity of static acceleration due to gravity of the Earth, an accelerometer may provide data as to the angle the object is tilted with respect to the Earth, the angle of which may be established in an x-, y-, and z-axis coordinate frame. However, where the object is accelerating in a particular direction, such that the acceleration is dynamic (as opposed to static), the accelerometer produces data which does not effectively distinguish the dynamic forces of motion from the force due to gravity by the Earth. Also as conventionally known in the art, a gyroscope is a device used to measure changes in orientation, based upon the object's angular velocity (rad/s) or angular acceleration (rad/s$^2$). A gyroscope may constitute a mechanical gyroscope, a micro-electro-mechanical system (MEMS) gyroscope, a ring laser gyroscope, a fiber-optic gyroscope, and/or other gyroscopes as are known in the art. Principally, a gyroscope is employed to measure changes in angular position of an object in motion, the angular position of which may be established in an x-, y-, and z-axis coordinate frame.

In an embodiment, sense elements from an IMU 112 mounted on the housing 111 of the device 110 may be fused with sense elements from IMU mounted on the work machine 200 or other position and/or orientation related inputs in an independent coordinate frame associated at least in part with the respective work machine 200. Outputs from a device IMU 112, alone or in combination with further outputs from one or more machine-based sensors, may be utilized to determine an orientation of the device housing 111 relative to the work machine 200 and thereby the ground surface, for example to confirm that the other components are operable to provide valid measurements in the context of a moisture estimation process as further described below.

The controller 206 of the work machine 200 may in some embodiments further receive inputs from and generate outputs to remote user devices 300 associated with a user via a respective user interface, for example a display unit 302 with touchscreen interface and associated input/output devices 306 and functionality. Data transmission, between for example a vehicle control system and a remote user interface, may take the form of a wireless communications system and associated components as are conventionally known in the art. In certain embodiments, a remote user interface and vehicle control systems for respective work machines 200 may be further coordinated or otherwise interact with a remote server 400 or other computing device for the performance of operations in a system 100 as disclosed herein.

The controller 206 may be configured to generate control signals for controlling the operation of respective actuators 208, for example such as described below with respect to an exemplary work machine of FIG. 2. The controller 206 may generate signals for indirect control of relevant actuators 208 via intermediate control units, associated with for example a machine steering control system, a machine implement control system, an engine speed control system, etc. Such control systems may be independent or otherwise integrated together or as part of a machine control unit in various manners as known in the art.

The controller 206 may include, or be associated with, the processor 206, as well as a computer readable medium, a communication unit, data storage such as for example a database network (not shown), and the aforementioned display unit 202 comprising or otherwise associated with a user interface or control panel. An input/output device, such as a keyboard, touch screen, or other user interface tool may be coupled to the controller 206 via the user interface so that the human operator may input instructions to the controller 206.

It is understood that the controller 206 described herein may be a single controller having all of the described functionality, or it may include multiple controllers wherein the described functionality is distributed among the multiple controllers.

Various "computer-implemented" operations, steps or algorithms as described in connection with the controller 206 or alternative but equivalent computing devices or systems can be embodied directly in hardware, in a computer program product such as a software module executed by the processor 204, or in a combination of the two. The computer program product can reside in RAM memory, flash memory, ROM memory, EPROM memory, EEPROM memory, registers, hard disk, a removable disk, or any other form of computer-readable medium known in the art. An exemplary computer-readable medium can be coupled to the processor 204 such that the processor 204 can read information from, and write information to, the memory/storage medium. In the alternative, the medium can be integral to the processor 204. The processor 204 and the medium can reside in an application specific integrated circuit (ASIC). The ASIC can reside in a user terminal. In the alternative, the processor 204 and the medium can reside as discrete components in a user terminal.

The term "processor" 204 as used herein may refer to at least general-purpose or specific-purpose processing devices and/or logic as may be understood by one of skill in the art, including but not limited to a microprocessor, a microcontroller, a state machine, and the like. A processor 204 can also be implemented as a combination of computing devices, e.g., a combination of a digital signal processor (DSP) and a microprocessor, a plurality of microprocessors, one or more microprocessors in conjunction with a DSP core, or any other such configuration.

The communication unit may support or provide communications between the controller 206 and external systems or devices, and/or support or provide communication interface with respect to internal components of the self-propelled work machine 200. The communications unit may include wireless communication system components (e.g., via cellular modem, WiFi, Bluetooth, or the like) and/or may include one or more wired communications terminals such as universal serial bus ports.

The data storage as further described below may, unless otherwise stated, generally encompass hardware such as volatile or non-volatile storage devices, drives, memory, or other storage media, as well as one or more databases residing thereon.

As noted above, various operations as disclosed herein, for example relating to non-contact ground moisture estimation, seeding, tillage or other earth working operations, and the like, may be executed via a controller 206 for a given work machine 200, wherein the controller may be a discrete device or integrated with a vehicle control system or equivalent. In various embodiments as initially noted above operations may further or in the alternative be executed via a distributed system 100 including one or more remote processors 304, 404, such as for example are associated with hosted servers 400 in a cloud computing platform or mobile user devices 300, independently or in association with a local controller 206 for each of one or more work machines 200a, 200b.

Each remote processor 304, 404 may be respectively or collectively associated with hosted cloud data storage 412 or distributed/third party data storage having for example ground moisture models 414, work models 416 relating to electronic worksite maps, planning information, work machine information, and the like retrievably stored thereon and collectively accessible for execution of operations and methods as disclosed herein.

Figure 2:
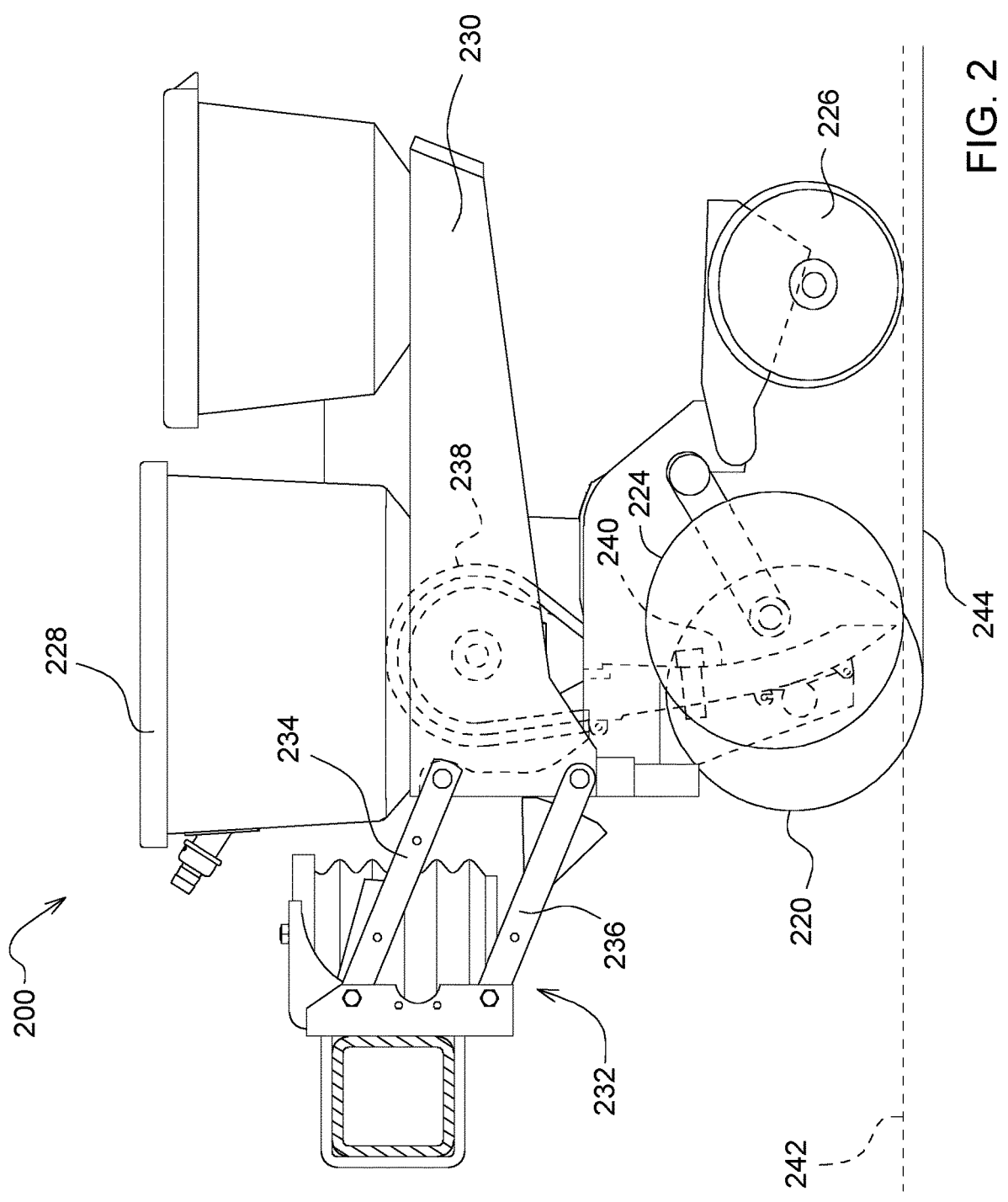
FIG. 2 is a side view representing an exemplary work machine according to an embodiment of the present disclosure.

Referring next to FIG. 2, an exemplary work machine 200 as disclosed herein may be a planter row unit configured to travel across a field while distributing seeds or other crop materials (e.g., roots, bulbs, or rhizomes) into the soil. However, as previously noted the scope of the present disclosure encompasses many alternative types of work machines 200 as may be appreciated by one of skill in the art.

In the illustrated embodiment, the planter row unit as work machine 200 can comprise a hopper 228 arranged in a generally upright position that is mounted to a frame 230. A parallel arm arrangement 232 comprising upper and lower arms 234, 236 and an actuation device can be mounted to the support frame 230 in a cantilever-like configuration, such that it extends outwardly and away from the frame 230. In some embodiments, the actuation device may be mounted to at least one of the upper or lower arm 234, 236 and can include mechanical, pneumatic, hydraulic, or other suitable actuators to apply lift and/or downforce on the planter row unit. A metering unit 238 having a generally circular configuration can be arranged beneath the hopper 228 and can be configured to distribute seeds received from the hopper 228 into a seed tube 240. The seed tube 240 directs the seeds received from the metering unit 238 to an opening 244 formed in the soil 242 by a ground engaging device 220. In some embodiments, a support member, which can be arranged to extend downwardly from the frame 230, is mounted adjacent the seed tube 240. The support member can be operably coupled to a ground engaging device 220 and can comprise a shank, vertical post, or other suitable support structure. To regulate the penetration depth of the ground engaging device 220, at least two gauge wheels 224 are mounted proximate the ground engaging device 220. A closing wheel assembly 226 can be arranged following the ground engaging device 220 and the gauge wheels 224 and is operable to close the opening 244 formed by ground engaging device 220.

Figure 4:
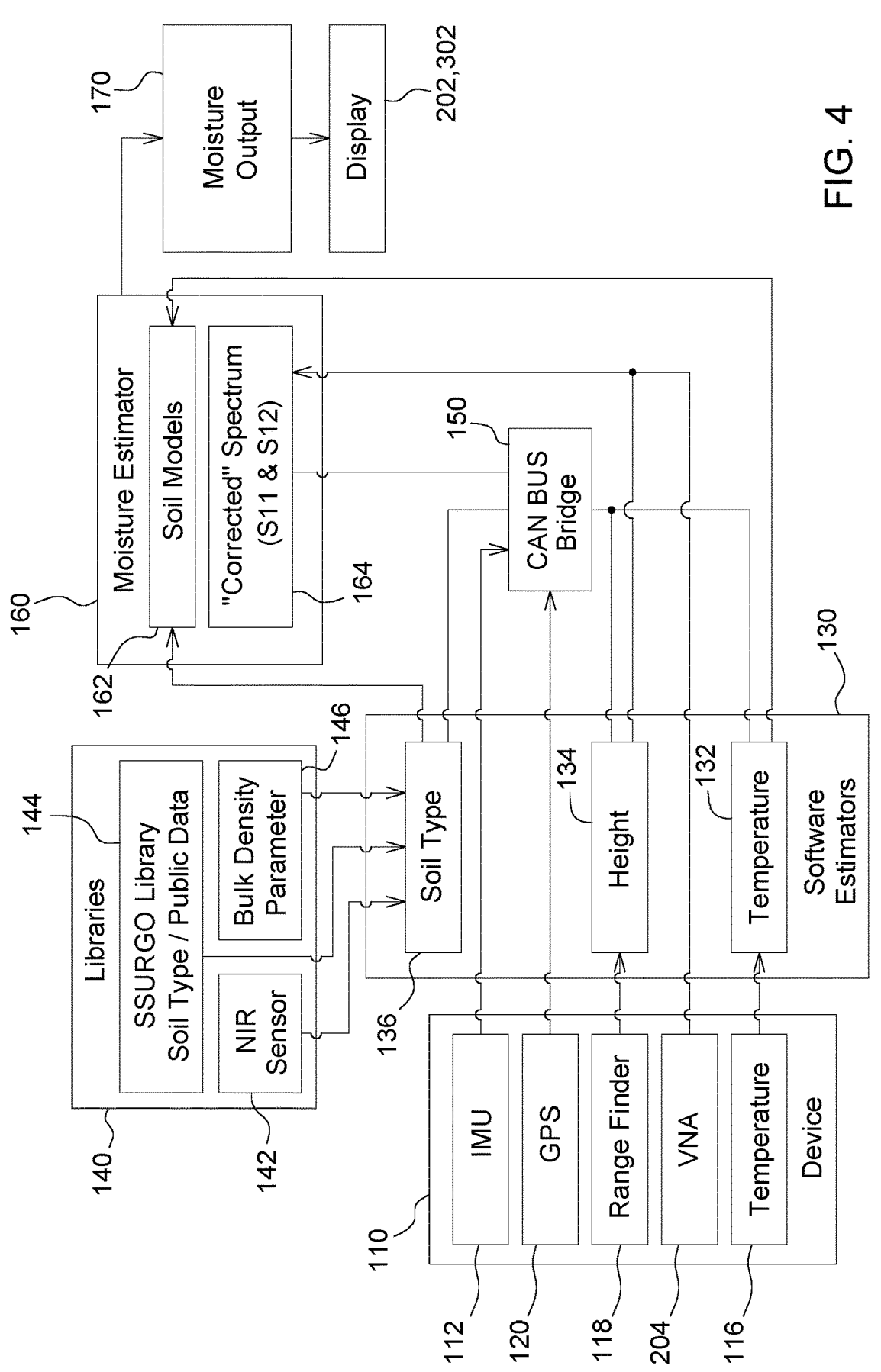
FIG. 4 is a block diagram representing exemplary data sources, logic, and software modules in a non-contact ground moisture detection system or device according to an embodiment of the present disclosure.

Referring next to FIGS. 3 and 4, various data sources and program modules may be described in relation to an embodiment of a system 100, device 110, and/or method 500 of the present disclosure.

As represented in FIG. 3, each of the IMU 112, directional antenna 114 (or antennas 114), temperature sensor 116, and depth sensor/range finder 118 are mounted to a housing 111, which is further mounted to the work machine 200. The housing 111 may be modular in nature, or in some embodiments may be permanently affixed or even integral to the frame of the work machine 200. The housing 111 may comprise a simple bracket to which the aforementioned components are mounted and/or integrally fixed, or may define an interior containing one or more of the aforementioned components and having apertures as needed for the components to provide their respective measurements while being relatively protected from environmental impacts during operation.

Figure 7:
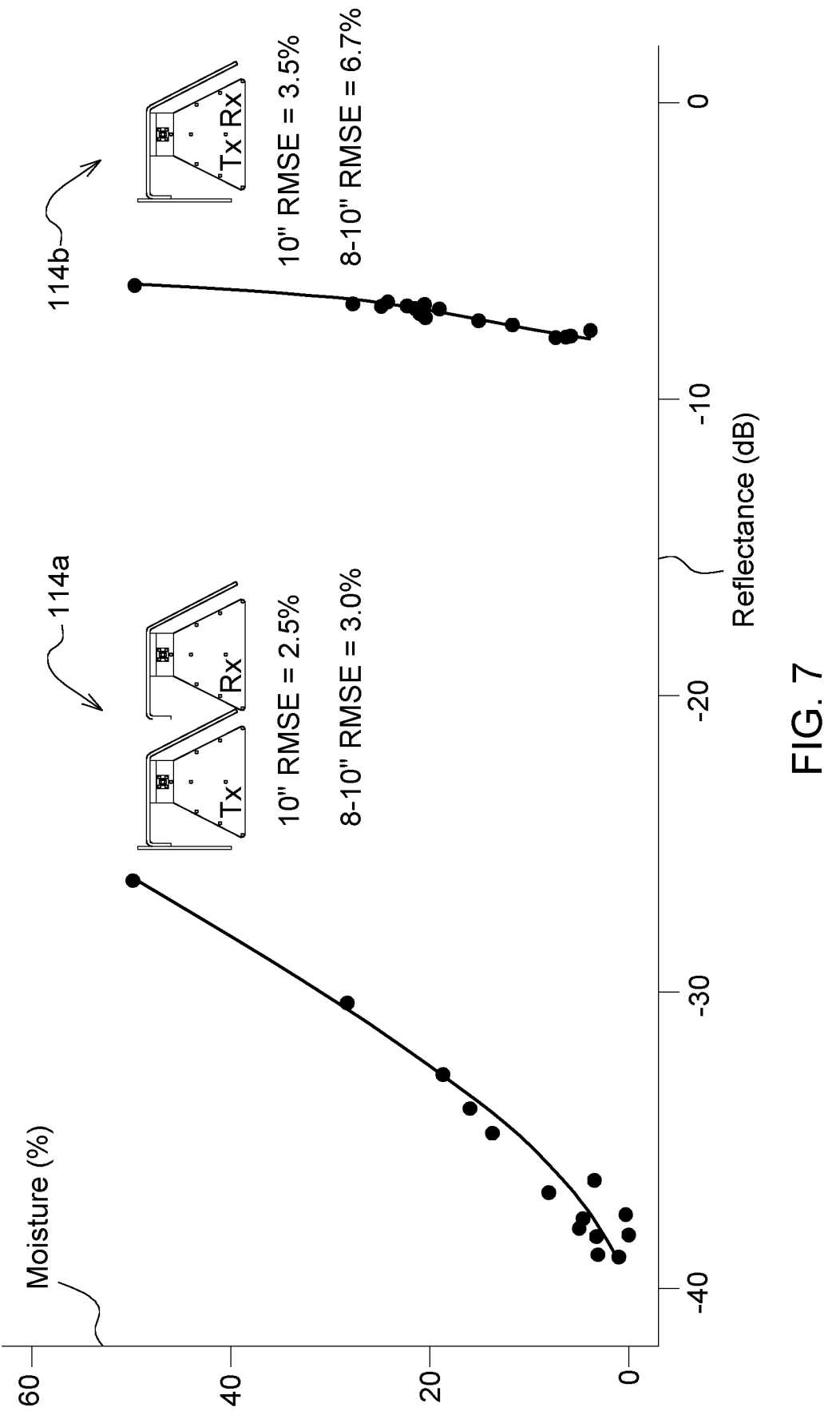
FIG. 7 is a graphical diagram representing exemplary test data for measured signal reflectance with respect to moisture levels.

The device 110 as illustrated is arranged to define a 25 cm air gap between the directional antenna(s) 114 and a surface of the ground traversed by the work machine 200, but alternative heights may be contemplated depending on the context, configuration, etc. As represented in FIG. 7, testing has indicated a root mean square error (RMSE) that is reduced for air gaps of 25 cm (~10 in.) with respect to smaller air gaps (e.g., 8-10 in.) when measuring moisture levels as a function of reflectance. Also, the RSME is further reduced in dual antenna configurations, wherein a first antenna is utilized for emission of RF energy while a second antenna is utilized for reflected RF energy, but single antenna configurations may be more practical due to reduced cost and complexity, and either configuration is considered as within the scope of a device 110 according to the present disclosure.

In the embodiment illustrated in FIG. 4, the data sources associated with the device 110 include an IMU 112, GPS transceiver 120, depth sensor/range finder 118, VNA 204, and temperature sensor 116. It may be understood that one or more of the data sources, such as the GPS transceiver 120 for example, may be located separately from the device 110 while providing the requisite functionality for the downstream processing.

Various data sources associated with the device 110 provide outputs to software estimators 130 which may be configured to transform, convert, or otherwise process the output signals to generate values represented thereby for use by a moisture estimator 160. The software estimators 130 and the moisture estimator 160 may in some embodiments be part of the controller 206, or discrete components such as microcontrollers separate from the other processing units described herein. The software estimators 130 and the moisture estimator 160 may in some embodiments be integrated with each other, or fully or partially discrete in configuration and functionality. The software estimators 130 as shown perform such data processing on the output signals from the depth sensor 118 and the temperature sensor 116 to generate a height value 134 and a temperature value 132, respectively. Output signals from the IMU 112 and the GPS transceiver 120 in the example shown are provided to the moisture estimator 160 via one or more communication buses, for example a CAN bridge device 150 linking a plurality of respective bus networks.

The VNA 204 of the system 100 or device 110 serves as a source of radio frequency (RF) energy coupled to the one or more device antennas 114 which radiates the RF energy outward towards the ground and receives the reflected energy therefrom. Output signals from the VNA 204 may be provided, for example along with the height values 134, for generation of a corrected frequency spectrum 164. Scattering parameters, or other parameters relating to a reflection coefficient or return loss attributable at least in part to an input/output relationship between ports and reflecting power transfer, may be generated by the VNA itself and provided to the moisture estimator 160, or this functionality may be partially distributed or in some embodiments omitted. The VNA 204 may for example provide a windowing function to select, dynamically or programmatically in context, a target frequency or range of frequencies (e.g., as a preferably focused subset of the available frequency range) for a given hardware configuration, application, work area, portion of the work area, or the like, to potentially optimize data collection and avoid having to sweep across the entirety of an available frequency range for the respective antennas.

Data storage local to the work machine or otherwise remote, for example in association with a hosted cloud platform or third party sources, may include one or more libraries 140 which can be accessed for further inputs to the moisture estimator 160, for example ascertaining a soil type 136. Libraries 140 may include historical actual soil moisture measurements for a given work area, or explicit references to a soil type 136 associated with the work area. A soil type 136 and/or other relevant information may be determining using input data obtained using for example near infrared spectroscopy and associated sensors 142, a geodatabase 144 accessible for any preestablished soil geographic data relating to the work area, such as for example the USDA-NRCS Soil Survey Geographic (SSURGO) database, a soil bulk density database 146 accessible to provide relevant parameters for the moisture estimator 160, and the like.

In some embodiments, information regarding soil properties for a particular location may be utilized for determining an optimal target frequency or range of frequencies for the RF energy. For example, relative proportions of clay, silt, sand, and the like in a given area may have previously been established and capable of being utilized to identify optimal frequencies for use in clay loam, sandy loam, silty clay, etc., to provide meaningful reflectance values at various depths without needing to sweep across an unnecessarily broad range of frequencies.

The moisture estimator 160 applies inputs from the device 110, software estimators 130, libraries 140, and the like to selected soil models 162 and generates one or more moisture output signals, values, or the like 170, such as for example plant available volumetric water content (VWC), for display on one or more display units 202, 302, for work machine control, for downstream work planning, etc.

Figure 5:
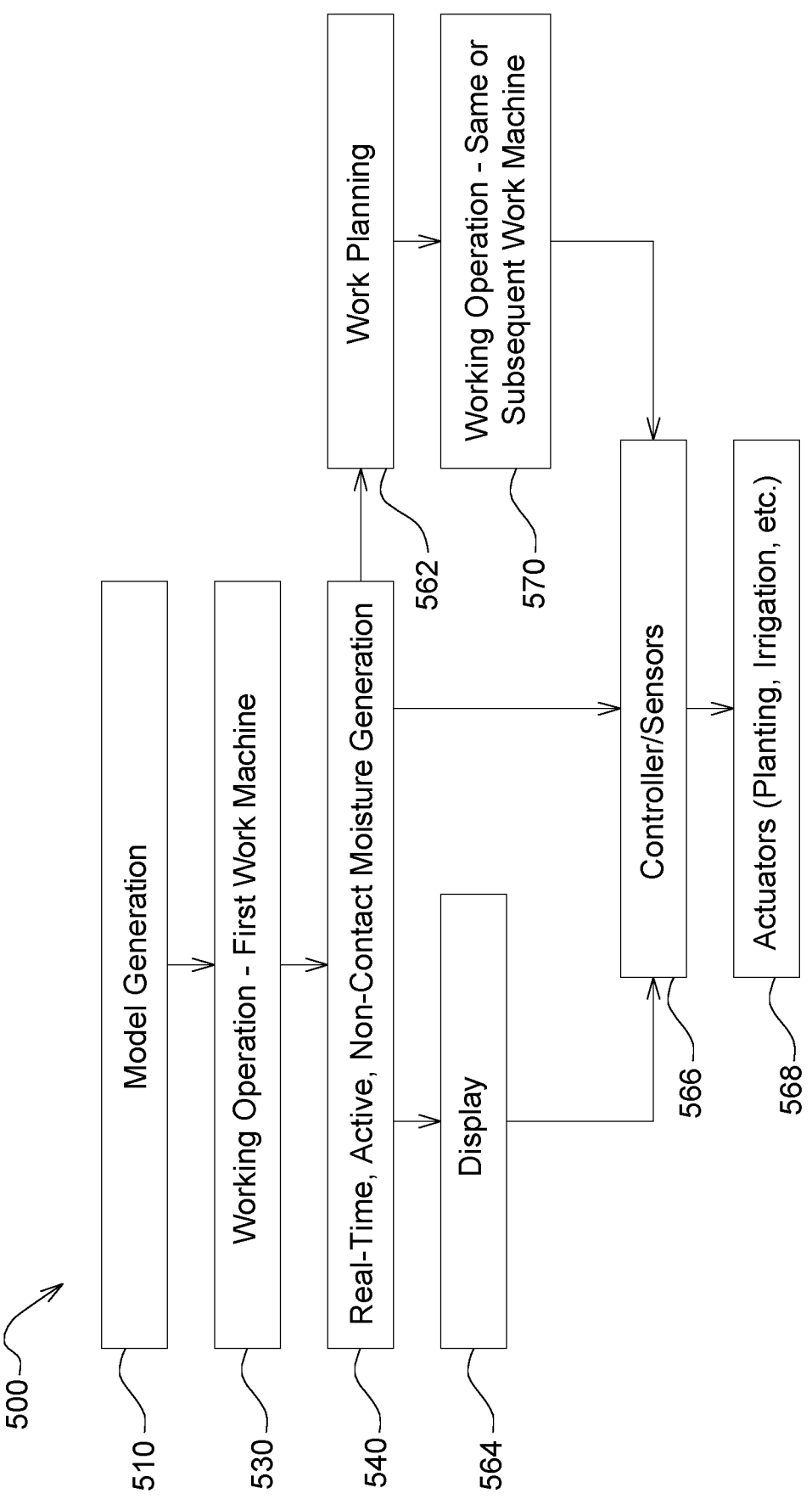
FIG. 5 is a flowchart representing an exemplary non-contact ground moisture estimation method according to an embodiment of the present disclosure.

In FIG. 5, the depicted flowchart represents an exemplary embodiment of a method 500 for non-contact ground moisture estimation using active radio frequency signals. The steps shown and described herein may in various alternative embodiments be performed in different order, or may in some contexts be combined into a single step, or even omitted altogether unless otherwise specifically noted herein.

In the embodiment shown, the method 500 includes the generation (e.g., development, training, testing) of one or more ground moisture models 510. Exemplary techniques for predictive model development may include machine learning, for example supervised and unsupervised learning, hard and soft clustering, classification, forecasting, and the like.

Figure 6:
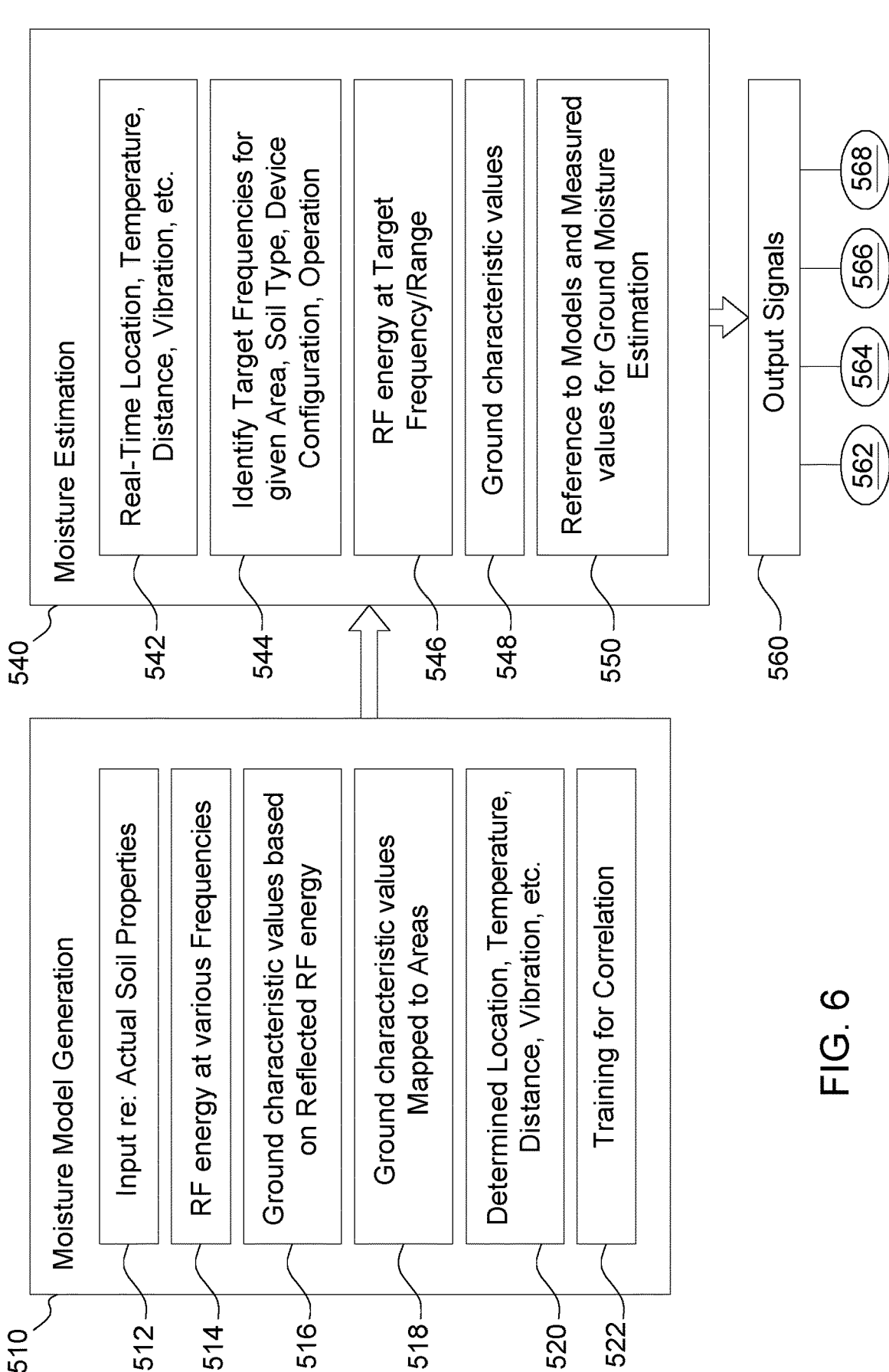
FIG. 6 is a flowchart representing a particular example of model generation and moisture estimation steps according to the method of FIG. 5.

With further reference to FIG. 6, an exemplary embodiment of moisture model generation includes obtaining or otherwise ascertaining inputs relating to actual soil properties 512. In various embodiments, the soil properties may preferably correspond to soil properties which may reasonably be obtained during subsequent real-time operations, such as for example through third party data corresponding to a given location determined via GPS, sensing by the work machine performing the moisture estimation operation or a previous work machine, sensors mounted on other units such as drones, etc. The soil properties may for example include a type of soil, soil components, conductivity, permeability, texture, porosity, and the like.

Generation of a moisture model 510 may further include emitting RF energy 514 at various frequencies towards test areas including the actual soil for which properties have been obtained or otherwise ascertained. The various frequencies may include frequencies across an entire range of available frequencies for the RF emitting configuration, a user-selected frequency or subset of the available frequencies, a frequency or subset of the available frequencies having already been learned and automatically applied by the system based on a priori knowledge regarding the current test conditions, etc.

Generation of a moisture model 510 may further include determining one or more ground characteristic values 516 based on the reflected RF energy, and mapping the determined ground characteristic values to respective test areas 518. In various embodiments, the mapped ground characteristic values may preferably correspond to moisture estimation and/or the setting of target frequencies/ranges of frequencies, and may primarily consist of reflectance values obtained for a ground surface and at one or more subterranean depths, but are not limited to such and various additional or alternative ground characteristic values may be identified as correlative and practically available through development of models according to the present disclosure.

Generation of a moisture model 510 may further include determining various additional inputs 520 to be associated with the actual soil properties and RF energy collection for a respective test area, including one or more of for example location, temperature, distance to ground surface, depth within the ground surface, vibration and/or orientation of the RF emitters and receivers, etc.

Generation of a moisture model 510 may further include training the model over various iterations to identify correlations for the various additional inputs and RF energy reflectance with respect to the actual measured soil properties. In various embodiments, the model may further or in the alternative be trained to identify target frequencies or a target range of frequencies best correlating associated reflectance measurements to observed soil properties at respective depths (e.g., including a ground surface and subterranean depths) and further in association with a range of real-time measurable conditions.

Discontinuities may relate at least in part to changes in the dielectric media (i.e., air versus soil having various properties). For example, air itself has a relatively small dielectric constant of approximately 1, and although dry soil also has a relatively small dielectric constant (approximately 2.5), the dielectric constant of water is quite large (approximately 80) in comparison to air and dry soil, and the moisture content of the soil is accordingly impacted by and at least indirectly determinable from the dielectric changes.

Initial moisture measurement may be derived from a surface reflection, based on a first sensed dielectric change, whereas reflections from one or more depths (discontinuities) may be used to estimate relative changes in moisture. For example, in a context wherein the soil beneath the ground surface in a particular work area or portion thereof comprises a relatively dry soil zone (e.g., located above a subterranean water line) and a relatively moist soil zone (e.g., located below the water line), the two zones may be characterized based on their relative moisture contents, with the moist soil zone having a greater moisture content and dielectric value than that of the dry soil zone under most conditions, further resulting in corresponding RF signal path delays indicative of the respective moisture conditions and dielectric values.

It may further be noted that signal reflection generally increases with decreases in frequency. Whereas a broad range of frequencies may be available for projection and reflection via the directional antenna(s) and as sourced via the VNA, it may be determinable through training of the moisture model that a relative subset of the available frequencies results in a highly accurate spectrum of meaningful results with respect to the expected characteristics in a given area and associated range of reflectance values, while substantially reducing the operating requirements.

In an embodiment, a machine learning moisture estimation model 414 may include variable governing parameters which are optimized during training to better simulate (or approximate in a particular simulation) observed real-life performance data corresponding to an input dataset (e.g., soil properties, characteristic values such as RF reflectance, temperature, etc.). Such variables may comprise hyperparameters that may initially be set (e.g., user-specified) before training. Tuning of the hyperparameters, or in other words optimizing the values thereof, follows during training to obtain a set of values for the hyperparameters corresponding to an accurate input-output mapping of the model for the training dataset. In various embodiments, tuning of parameters may be performed automatically during or between training iterations, manually based on user selection via a system interface, or combinations thereof.

Returning to FIG. 5, with models having been generated to at least a minimum confidence level, and without precluding further development and training of the models over time, the method 500 may proceed in association with a current working operation 520 for at least a first work machine, wherein a real-time active, non-contact moisture estimation is conducted 540.

With reference again to FIG. 6, an exemplary embodiment of moisture estimation includes measuring, obtaining, or otherwise ascertaining current, substantially real-time, inputs 542 including one or more of for example a current location, temperature, distance to ground surface, vibration and/or orientation of the RF emitters and receivers, etc.

Moisture estimation in the embodiment of FIG. 6 may further include identifying target frequencies (e.g., a target range of frequencies) 544 at which RF energy is to be emitted towards a ground surface. The target frequencies may be identified based on relevant factors which may include one or more of a given area, soil type, device configuration, work operation, etc.

Moisture estimation in the embodiment of FIG. 6 may further include emitting RF energy towards the ground surface at the target frequency (or across the target frequency range), and further receiving the reflected RF energy 546. In an embodiment, a first antenna may be utilized to emit the RF energy and a second antenna may be utilized to receive the reflected RF energy, but alternatively the same antenna may be utilized for both emission and reception of the RF energy.

Moisture estimation in the embodiment of FIG. 6 may further include determining one or more ground characteristic values 548 from analysis of the reflected RF energy, which may for example supplement other ground characteristic values which may be available by reference to other data sources.

Moisture estimation in the embodiment of FIG. 6 may further include reference to one or more selected moisture models as previously developed and trained, and further reference to the current inputs and ground characteristic values for ground moisture estimation 550.

Output signals representative of the estimated ground moisture values may further be generated 560, for example to be provided as inputs to a work planning module 562, to provide image data 564 for presentation and/or user interface on one or more displays 202, 302, to a controller as a basis for work machine control 566, and/or to one or more sensors associated with the work machine for calibration/ confirmation of measured values 566.

In an embodiment, a cross sectional view of a work area, or a representative portion thereof, may be graphically represented on the display unit with indicia representing the one or more moisture values at the respective ground surface and one or more depths. In addition, or alternatively, an overhead view of the work area, or a representative portion thereof, may be graphically represented on the display unit with indicia corresponding to relative moisture values for the respective ground portions.

One exemplary user interface may represent a work area having multiple portions, each of which have respectively measured reflectance values at one or more depths, and respectively measured and/or estimated moisture values at the one or more depths. Such values may be graphically represented using indicia such as shown in FIGS. 8A and 8B, or preferably using color coding such as for example with underlying color swaths representing measured reflectance values throughout the work area and colored dots representing the moisture levels, or vice versa.

Figures 9A, 9B:
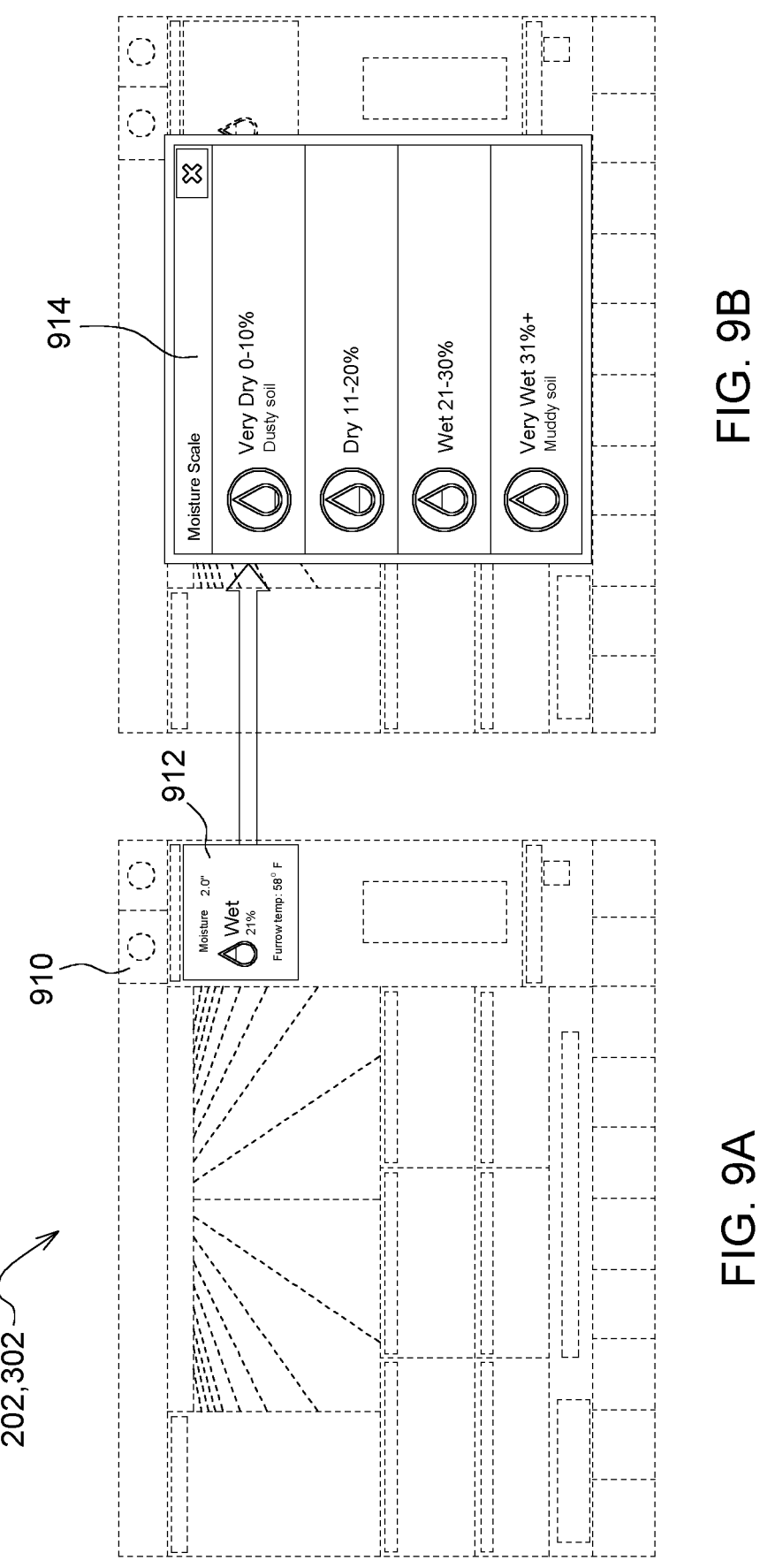
FIGS. 9A and 9B are graphical diagrams representing a main page of a user interface for an operator of a work machine, and a breakout screen selectively displayed and including moisture level indications for a highlighted portion of the work area, respectively.

As illustrated in FIGS. 9A and 9B, an exemplary user interface 910 may include any number of representative images of a work area, data corresponding to current conditions or operating parameters, and in various embodiments one or more interface portions displaying information corresponding to determined soil parameters which may include moisture levels at the surface and/or one or more relevant depths. In an embodiment, upon user selection of a frame 912 including data and indicia (e.g., graphical icons, color coding) comprising a current moisture level (e.g., as a percentage) and a representative descriptor for the current moisture level (e.g., "wet"), a pop-up frame 914 may be generated to provide further information regarding the data and/or indicia. For example, as illustrated in FIG. 9B an information frame may be presented to clarify the descriptors and corresponding symbols for each of a plurality of moisture levels along a predetermined moisture scale.

In an embodiment, a work planning module 562 may generate a work plan for real-time control of a work operation 570 of the same work machine as the measured values and reflected RF energy is being provided for moisture estimation. The work planning module 562 may further or in the alternative generate a work plan for subsequent control of a work operation of the same or different work machine relating to the same work area being measured in the moisture estimation stage.

Output signals relating to moisture estimation, alone or in the context of further generated work plan, may be utilized by the controller to provide control signals to one or more actuators associated with the work machine 568 for controlling operations such as seeding, tilling, irrigation, etc.

As one example, a work plan may be generated in the context of a uniform emergence model which, e.g., correlates target seed depth to plant available moisture, wherein the planting depth may be dynamically controlled based on real-time moisture estimation in the work area (e.g., field) or based on previously estimated moisture characteristics which are mapped to respective locations in the work area.

As another example, a work plan may be generated in the context of an irrigation model which, e.g., seeks to provide a uniform and/or seasonably appropriate plant available moisture throughout a work area or portion thereof, wherein an amount and/or frequency of irrigation applied may be dynamically controlled based on real-time moisture estimation in the work area (e.g., field) or based on previously estimated moisture characteristics which are mapped to respective locations in the work area.

Additional examples of work plans may relate, e.g., to spraying, harvesting, earth moving, road construction, and various other applications and operations potentially impacted by ground moisture as may be appreciated by one of skill in the art.

In some embodiments, components of a work plan may be utilized for optimizing frequency selection or other aspects of the moisture estimation stage. For example, a target range of frequencies may be determined in the real-time moisture estimation stage based at least in part on a range of expected target planning depths, wherein the target planting depths are further determined based on a stored uniform emergence model correlating the one or more moisture values and expected crop growth at respective planting depths.

In various embodiments, output signals conveying information such as estimated moisture values, in association with a location, conditions, measured inputs, and the like, may provide feedback for continued development, training, testing, etc., of the moisture estimation models via observation and machine learning.

In various embodiments, output signals conveying information such as estimated moisture values, in association with a location, conditions, measured inputs, and the like, may provide feedback to one or more sensors associated with the work machine for optional use in condition measurement, calibration, confirmation, etc. For example, a work machine may be configured to estimate soil properties in real time based on one or more machine operating parameters during an earth working operation, wherein estimated soil moisture information (optionally further including measured values such as temperature, etc.) may be used as feedback to assist or confirm in these real-time estimations or in development of models therefor. This process may be synergistic in nature, as real time soil property estimations by the work machine controller, if sufficiently credible, may be provided to confirm or correct soil properties from third party sources as utilized by the soil moisture estimation systems and methods as disclosed herein.

As used herein, the phrase "one or more of," when used with a list of items, means that different combinations of one or more of the items may be used and only one of each item in the list may be needed. For example, "one or more of"

item A, item B, and item C may include, for example, without limitation, item A or item A and item B. This example also may include item A, item B, and item C, or item B and item C.

Thus, it is seen that the apparatus and methods of the present disclosure readily achieve the ends and advantages mentioned as well as those inherent therein. While certain preferred embodiments of the disclosure have been illustrated and described for present purposes, numerous changes in the arrangement and construction of parts and steps may be made by those skilled in the art, which changes are encompassed within the scope and spirit of the present disclosure as defined by the appended claims. Each disclosed feature or embodiment may be combined with any of the other disclosed features or embodiments.

What is claimed is:

1. A method for non-contact moisture estimation, comprising:

in a model generation stage:

receiving first input data representing actual soil properties comprising moisture values at a training ground surface and one or more corresponding ground depths of a respective ground portion;

emitting radio signals associated with a first range of frequencies toward the training ground surface, and determining one or more characteristic values for the ground portion based on received reflections of the radio signals;

receiving second input data representing temperature, a distance between the training ground surface and a source of the radio signals, and a vibration of the source of the radio signals;

iteratively training a model in data storage comprising correlations between the first data, the one or more characteristic values at corresponding frequencies, and at least a subset of the second data; and in a real-time moisture estimation stage, with respect to a current ground surface associated with a current ground portion:

receiving third input data representing temperature, a distance between the current ground surface and a source of radio signals, and a vibration of the source of the radio signals;

identifying, via a vector network analyzer operatively linked to the source of the radio signals, a target range of frequencies as a subset of the first range of frequencies;

emitting radio signals associated with the target range of frequencies toward the current ground portion, and determining one or more characteristic values for the current ground portion based on received reflections of the emitted radio signals;

estimating, via the determined one or more characteristic values and further reference to the iteratively trained model, one or more moisture values for the current ground surface and one or more corresponding ground depths for the current ground portion; and generating an output signal corresponding to the estimated one or more moisture values, wherein the output signal is configured to be utilized by a controller to provide a control signal for controlling an operation.

2. The method of claim 1, wherein the real-time moisture estimation stage is executed during operation of a work machine traversing a work area comprising a respective current ground surface for each of a plurality of current ground portions.

3. The method of claim 2, wherein the source of the radio signals and one or more sensors configured to provide the third input data are mounted to a common housing associated with the work machine.

4. The method of claim 2, wherein the output signal comprises a control signal to one or more actuators for controlling a respective planting depth with respect to each of the plurality of current ground portions, wherein a target planting depth is determined based on the estimated one or more moisture values.

5. The method of claim 4, wherein the target range of frequencies is determined in the real-time moisture estimation stage based at least in part on a range of expected target planning depths.

6. The method of claim 4, wherein the target planting depth is further determined based on a stored uniform emergence model correlating the one or more moisture values and expected crop growth at respective planting depths.

7. The method of claim 2, wherein the output signal comprises a feedback signal to one or more sensors associated with the work machine, or to a controller for determining one or more values based on respective outputs from the one or more sensors and the one or more estimated moisture values.

8. The method of claim 1, wherein the target range of frequencies is determined in the real-time moisture estimation stage based at least in part on the received third input data.

9. The method of claim 1, wherein the target range of frequencies is determined in the real-time moisture estimation stage based at least in part on an ascertained configuration of the source of the radio signals and/or a receiver of the radio signals.

10. The method of claim 9, wherein the radio signals are emitted from, and received by, a single antenna in functional communication with the vector network analyzer.

11. The method of claim 9, wherein the radio signals are emitted from, and received by, respective antennas in functional communication with the vector network analyzer.

12. The method of claim 1, wherein:

the model generation stage is executed at least in part using a first work machine traversing a work area comprising a respective current ground surface for each of a plurality of current ground portions;

the real-time moisture estimation stage is executed during operation of a second work machine subsequently traversing the work area; and the target range of frequencies is determined in the real-time moisture estimation stage based at least in part on measured soil properties for the work area during the model generation stage.

13. The method of claim 12, wherein the target range of frequencies is determined in the real-time moisture estimation stage based at least in part on mapped soil properties for respective portions of the work area.

14. The method of claim 1, wherein:

the real-time moisture estimation stage is executed during operation of a first work machine traversing a work area comprising a respective current ground surface for each of a plurality of current ground portions;

the output signal is provided to a computing device via a communications network, wherein a work plan is generated for the work area based at least in part on the estimated moisture values for each of the plurality of current ground portions; and

the work plan is provided for utilization by a second work machine associated with the work area.

15. The method of claim 14, wherein the output signal comprises a control signal to one or more actuators associated with the second work machine for controlling a respective planting depth with respect to each of the plurality of current ground portions, wherein a target planting depth is determined as part of the work plan.

16. The method of claim 15, wherein the target range of frequencies is determined in the real-time moisture estimation stage based at least in part on a range of expected target planning depths.

17. The method of claim 15, wherein the target planting depth is further determined based on a stored uniform emergence model correlating the one or more moisture values and expected crop growth at respective planting depths.

18

18. The method of claim 14, wherein the output signal comprises a control signal to one or more actuators associated with the second work machine for controlling a respective irrigation value with respect to each of the plurality of current ground portions, wherein a target irrigation value is determined as part of the work plan.

19. The method of claim 1, wherein the output signal is provided to a display unit, and a cross sectional view of at least part of the work area is graphically represented on the display unit with indicia representing the one or more moisture values at the respective ground surface and one or more depths.

20. The method of claim 1, wherein the output signal is provided to a display unit, and an overhead view of at least part of the work area is graphically represented on the display unit with indicia corresponding to relative moisture values for the respective ground portions.

* * * * *